(12) United States Patent
Anitua Aldecoa (10) Patent No.: US 8,993,733 B2
(45) Date of Patent: Mar. 31, 2015

(54) PROCEDURE FOR OBTAINING A COMPOSITION CONTAINING GROWTH FACTORS FROM A BLOOD COMPOUND, AND COMPOSITION OBTAINED BY SAID PROCEDURE

(76) Inventor: Eduardo Anitua Aldecoa, Vitoria (ES)

( * ) Notice: Subject to any disclaimer, the term of this patent is extended or adjusted under 35 U.S.C. 154(b) by 0 days.

(21) Appl. No.: 13/560,389

(22) Filed: Jul. 27, 2012

(65) Prior Publication Data

US 2013/0030161 A1 Jan. 31, 2013

(30) Foreign Application Priority Data

Jul. 29, 2011 (ES) .................................. 201100867

(51) Int. Cl.
*C07K 14/475* (2006.01)
*C07K 1/34* (2006.01)
*A61K 38/18* (2006.01)

(52) U.S. Cl.
CPC .............. *A61K 38/18* (2013.01); *C07K 14/475* (2013.01)
USPC ...................................................... 530/399

(58) Field of Classification Search
None
See application file for complete search history.

(56) References Cited

U.S. PATENT DOCUMENTS

| 5,871,997 | A | 2/1999 | Rother et al. | |
|---|---|---|---|---|
| 7,229,645 | B2 * | 6/2007 | Maa et al. | 424/489 |
| 2006/0004189 | A1 * | 1/2006 | Gandy | 530/399 |

FOREIGN PATENT DOCUMENTS

| EP | 1066838 | 10/2001 |
|---|---|---|
| EP | 2077118 | 8/2009 |
| WO | 00/44314 | 8/2000 |
| WO | 03026786 | 4/2003 |
| WO | 2008048228 | 4/2008 |
| WO | 2008078189 | 7/2008 |
| WO | 2010/130851 | 11/2010 |

OTHER PUBLICATIONS

Ayache, et al., Comparison of proteomic profiles of serum, plasma, and modified media supplements used for cell culture and expansion, Journal of Translational Medicine, 2006, pp. 1-12, vol. 4, No. 40.
Furlan, et al., Inulin like lyoprotectant of bovine plasma proteins concentrated by ultrafiltration, Food Research International, 2010, pp. 788-796, vol. 43.
Huang, et al., Purification and Properties of Epithelial Growth Inhibitor (EGI) from Human Platelets: Its Separation from Type beta Transforming Growth Factor (TGF-beta)1, J. Biochem., 1986, pp. 687-696, vol. 100.
Pietramaggiori, et al., Freeze-dried platelet-rich plasma shows beneficial healing properties in chronic wounds, Wound Repair and Regeneration, 2006, pp. 573-580, vol. 14, No. 5.
Yang, et al., Preparation of a respiratory syncytial virus human reference serum for use in the quantitation of neutralization antibody, Biologicals, 2007, pp. 183-187, vol. 35.
Search report dated Nov. 8, 2011 for Spanish application No. 201100867.
International search report for PCT/ES2012/000196 mail date May 12, 2012.

* cited by examiner

*Primary Examiner* — Brian J Gangle
*Assistant Examiner* — Andrea McCollum
(74) *Attorney, Agent, or Firm* — Browdy and Neimark, PLLC (57) ABSTRACT

Procedure for obtaining a composition that contains growth factors, which comprises the steps of heat-treating a platelet-rich plasma or the supernatant of a platelet-rich plasma that contains released growth factors in order to increase its temperature, for eliminating the complement and reducing the immunoglobulins present therein, and lyophilizing the plasma or supernatant in order to obtain a final dry composition that can easily be transported, handled and stored, thereby facilitating periodic or chronic treatments with blood compounds. It has been shown that when the final dry composition is resuspended, a once again humid composition is obtained that maintains its biological properties intact.

18 Claims, 11 Drawing Sheets

PROCEDURE FOR OBTAINING A COMPOSITION CONTAINING GROWTH FACTORS FROM A BLOOD COMPOUND, AND COMPOSITION OBTAINED BY SAID PROCEDURE

TECHNICAL FIELD

The invention relates to a procedure for obtaining a composition that contains growth factors, with or without the presence of cellular blood components (platelets, erythrocytes and white blood cells), from a blood compound. The invention also relates to the composition containing growth factors that is obtained by means of said procedure.

PRIOR ART

The preparation of blood compounds containing growth factors that are obtained from the patient's blood is widely known in the prior art. Said blood compounds containing growth factors have shown to possess very important biological properties, especially when it comes to triggering and stimulating tissue regeneration, reducing pain in certain types of diseases and disorders, and other multiple uses.

By way of example, patent application WO0044314A1, by the same applicant as the one of the present invention, relates to a method for the preparation of a gel from autologous blood plasma, the gel being rich in growth factors and obtained from the patient's own blood; said procedure was updated in the more recent patent application WO2010130851A2, also by the present applicant. Both procedures share common steps such as the centrifugation of the patient's blood, the separation of a platelet-rich plasma and the addition of calcium chloride to the platelet-rich plasma in order to activate the plasma (i.e., to cause growth factors contained in the plasma platelets to be released) and coagulate the plasma until it acquires a gel-like consistency.

Another known example is disclosed in patent ES2221770B2. The patent refers to a procedure for the preparation of a blood compound that is rich in growth factors and has very beneficial biological properties. In this case, the compound is in liquid form. In particular, the compound is a supernatant of a growth-factor-rich blood plasma that is obtained from the supernatant liquid phase that appears after inducing coagulation and the subsequent retraction of said growth-factor-rich plasma. This patent also describes various uses of the supernatant, foremost among which is its use (due to its liquid consistency) as eye drops for the treatment of eye diseases and disorders.

A plasma gel containing growth factors, a supernatant or generally any autologous blood compound prepared according to the methods known to prior art, irrespective of the application they are meant to be used for, present the disadvantage of having to be applied immediately, before they loose their biological properties. This necessity is particularly critical when the blood compound contains released growth factors. Thus, blood compounds are not prepared for enduring for long periods of time at room temperature and their immediate application is recommended (in the case of supernatants, within eight hours of their preparation) in order to avoid the degradation and denaturation of the proteins and growth factors or a possible bacterial contamination of the product.

The need of immediate use of autologous blood compounds has so far not been limiting, as the applications in which they have been used (tissue regeneration, cell culture, acute applications or even weekly or semi-monthly, etc. applications) have been compatible with said immediate use.

However, new potential applications of autologous blood compounds with growth factors are emerging nowadays that require continuous infiltration or application of the compound, with reduced time intervals between doses. The use of autologous blood compounds (gel, supernatant, etc.), as they are currently known, in these new applications would require a continuous blood extraction from the patient. Obviously, this circumstance would very negatively affect the patient's quality of life and the feasibility of long-term treatments of chronic or degenerative diseases.

There are numerous examples of chronic or degenerative diseases that could be treated with blood compounds containing growth factors, but are currently not, as blood compounds must be immediately used and cannot be stored: eye, central nervous system and degenerative joint diseases, and generally all those diseases or disorders that require chronic or repetitive administration of the blood compound containing growth factors.

The afore-mentioned diseases include, but are not limited to, the following: systemic lupus erythematosus, a chronic autoimmune disease that affects the connective tissue, characterized in that the immune system produces inflammation and tissue damage, specifically attributed to the binding of antibodies to organ cells and the formation of antigen-antibody complexes; Sjögren's syndrome, a systemic autoimmune disease that mainly affects the exocrine glands leading to dryness; dermatomyositis, a disease of the connective tissue that leads to muscle and skin inflammation; rheumatoid arthritis, a systemic autoimmune disease that provokes chronic inflammation, mainly of the joints, progressively leading to destruction with various degrees of deformity and functional disability. Presently there are studies showing that an autologous blood composition containing growth factors could most efficiently slow down all these diseases if were able to be regularly applied to the patient.

The objective of the present invention is to offer a procedure for obtaining a composition containing growth factors from platelet-rich plasma or a supernatant of a platelet-rich plasma, wherein the procedure allows for the procurement of a composition that can be stored during long periods of time and can easily be transported, so that the composition is suitable not for immediate use but for being applied at any given time or when deemed necessary. Thus, the procedure according to the invention shall allow for the procurement of a composition that may be used on a regular basis in therapeutic approaches of chronic diseases, without the need of constant blood extractions from the patient, thereby improving the quality of the patient's life.

Another objective of the present invention is that the composition obtained from the procedure according to the invention maintains its biological properties intact.

Another objective of the present invention is that the composition obtained from the procedure according to the invention maintains improved biological properties that are particularly indicated for the treatment of autoimmune diseases.

BRIEF DESCRIPTION OF THE INVENTION

The object of the present invention is a procedure for obtaining a composition that contains growth factors, that comprises several steps.

Firstly, the procedure comprises the step of being provided with a platelet-rich plasma or a supernatant of a platelet-rich plasma that contains released growth factors. The platelet-rich plasma or the supernatant of a platelet-rich plasma may be of various types: a plasma gel rich in growth factors and obtained according to the technique disclosed in WO0044314A1, WO2010130851A2 or any other applicable technique; a supernatant obtained as the liquid component that appears after inducing coagulation and subsequent retraction of a platelet-rich blood plasma, where said supernatant may be obtained, for example, according to the technique described in patent ES2221770B2; or generally any platelet-rich plasma.

Subsequently, the procedure according to the invention comprises the step of heat-treating the platelet-rich plasma or the supernatant of a platelet-rich plasma, during which the temperature of the blood compound is increased. The heat treatment allows for the elimination of the complement and reduces the presence of some of the immunoglobulins most frequently found in the plasma or supernatant that play a critical role in cross reactions from an immunological point of view. Said elimination or considerable reduction of the complement present in the plasma or supernatant enhances the applicability of the product to treating diseases of the immune system enormously.

Additionally, the procedure according to the invention comprises a step in which the blood compound is lyophilized in order to obtain a final composition that is practically devoid of humidity.

According to the invention, it makes no difference in which order the steps of heat-treating and lyophilizing the plasma or supernatant are carried out, i.e. they may be performed in any order.

In addition, the procedure according to the invention may comprise a step of filtering the platelet-rich plasma or supernatant of a platelet-rich plasma. Said step is carried out before lyophilizing, but not necessarily immediately before lyophilizing; for instance, in case the heat-treating is performed prior to lyophlization, the filtering step will be performed before the heat-treating.

The procedure for obtaining a composition from an autologous platelet-rich plasma or a supernatant of an autologous platelet-rich plasma allows for a final dry composition that presents numerous advantages over the traditional humid plasma or supernatant. A significant advantage is that a dry composition is notably easier to handle and to transport than a humid compound (a liquid, a more or less viscous gel or any other consistency). Furthermore, since it does not contain water, the dry composition can be maintained in room temperature and can even be stored for unlimited time, as it is a product with long-term stability (and as a result its use may be postponed as it does not necessarily have to be used immediately after its preparation). Additionally, the fact that it is devoid of water eliminates the risk of it being contaminated. Another advantage of the dry composition is that it can rapidly be restored to its original state; this procedure can easily be performed on-site by simply resuspending the dry composition in any isotonic solvent routinely used (e.g. water).

It has been shown that an additional advantage of the dry composition according to the invention is that when the dry composition is resuspended in order to recover a humid state for the purpose of being administered, said resuspended composition preserves the biological properties of the humid plasma or supernatant before it underwent the procedure according to the invention. That is to say, the resuspended composition maintains an analogous concentration of growth factors with biological activity; additionally, the effects induced by the resuspended composition on cell proliferation, cell migration and chemotaxis and the autocrine and paracrine synthesis of growth factors are identical to those of the humid plasma or supernatant. This preservation of the biological properties is, among others, a result of the appropriate temperature applied to the product during the procedure according to the invention. On the other hand, the low temperature that is used in the various steps of the procedure ensures that any loss of volatile components contained in the plasma or supernatant that might occur during the procedure is kept at a minimum. Low temperatures also ensure a low risk of bacterial contamination and that the preparation does not suffer any alterations regarding enzymes (it is advantageous that enzyme-containing preparations, as is the case of the plasma or supernatant of the present invention, are handled at low temperatures in order to avoid damaging them).

Another extremely beneficial effect of the invention is that the dry composition, and therefore the final resuspended composition, is free of complement or contains a reduced amount thereof, thereby rendering the resuspended final composition particularly optimal for treating a number of autoimmune diseases.

All the foregoing allows for the dry composition to be used for non-immediate treatments, e.g. for treating chronic disorders on a regular basis, and in particular, chronic autoimmune diseases. This way, if the dry composition obtained according to the invention is stored, for example, in doses, then the chronic treatment with said composition turns into a very simple process: the chronic patient is able to carry their dose (in a container, for example) anywhere without fear or complications; for administering the dose, the patient simply has to moisten or resuspend it and, once the original humid consistency (liquid or other) has been restored, proceed to apply the composition.

All these particular characteristics and benefits associated with the composition obtained by the procedure according to the invention can be summarized as follows: optimal stability; a particular indication for a number of autoimmune diseases; simple, rapid and complete solubility; unlimited storing; adequate protection against external harmful factors and rapid availability for use.

Another object of the present invention is a composition that contains growth factors, obtained by the procedure according to the invention. Said composition presents all the advantages described above.

BRIEF DESCRIPTION OF THE DRAWINGS

Details of the invention are depicted in the accompanying figures, which are intended to be illustrative and non-limiting.

DETAILED DESCRIPTION OF THE INVENTION

The object of the present invention is a procedure for obtaining a composition that contains growth factors, with or without the presence of hematic cellular components (platelets, erythrocytes and white blood cells), that comprises the following steps:

a) Being provided with a platelet-rich plasma or a supernatant of a platelet-rich plasma containing released growth factors, the plasma or supernatant being prepared according to any applicable preparation procedure. A plasma or supernatant with released growth factors is one in which the growth factors contained in the platelets have been released and the coagulation cascade has been activated, all by means of an applicable agent (calcium chloride, thrombin, calcium salts, other agents containing divalent ions or combinations thereof, or any other system that activates coagulation), thereby obtaining a product that is rich in proteins and both plasmatic and platelet-related growth factors. The plasma or supernatant may be of various types: a growth-factor-rich plasma gel obtained according to the technique disclosed in WO0044314A1, WO2010130851A2 or other applicable technique; a supernatant obtained as the liquid component that appears after inducing coagulation and subsequent retraction of blood plasma, where said supernatant may be obtained, for example, according to the technique described in patent ES2221770B2; or, in general, any plasma or supernatant that has been obtained by any given procedure.

b) Applying a heat treatment to the plasma or supernatant in order to eliminate the complement and reduce the presence of some of the immunoglobulins most frequently found in plasmas or supernatants, which play a critical role in cross reactions from an immunological point of view. Said elimination or considerable reduction of the complement present in the plasma or supernatant enormously benefits the applicability of the blood compound to diseases of the immune system. It is known that the presence of the complement system in a blood compound may cause adverse effects as it is involved in the overstimulation of the immune system and in many cases in the symptomatology itself of the disease that the blood compound is meant to treat. The plasma complement is related to numerous alterations such as possible adverse reactions in autoimmune diseases (lupus erythematosus, arthritis, etc.) mediated by complement (classical complement pathway) or adverse reactions from chronic inflammatory diseases also mediated by complement. In addition, part of the complement factors increase inflammation and phagocytosis and induce lysis of cells and microorganisms. In turn, among the immunoglobulins (Ig) most frequently found in blood compounds is the immunoglobulin IgG, some of which's main biological functions are the fixation of the complement, the binding to Fc receptors in phagocytic cells when opsonising particles during phagocytosis and the binding to receptors in NK cells during antibody-mediated cytotoxicity. This is why the elimination or considerable reduction of the complement present in the plasma or supernatant is such an important advantage for the application of the latter to diseases of the immune system. Heat treatment makes it possible to obtain a final composition that is adapted to the needs of patients with immune system disorders. As for the immunoglobulins, their total or partial reduction is important for patients with autoimmune diseases, as various IgGs take part in some of the acute rejection processes and therefore reducing their presence in the formulation helps to treat various types of tissues without risking a rejection or an acute immune reaction.

c) Lyophilizing of the plasma or supernatant in order to eliminate almost all of the water it contains and allow for the plasma or supernatant to pass from a humid state to a non-humid state that enables it to be stored for long periods of time.

Figure 14:
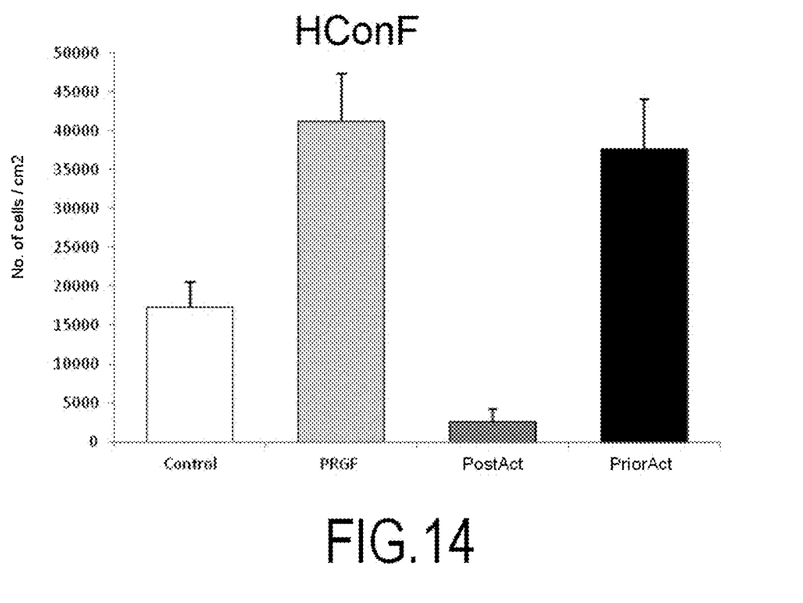
FIG. 14 shoes a graph of the concentration of primary cell cultures of human conjunctival fibroblasts (HConF) performed in three different media: an activated platelet-rich plasma that has not been heat-treated, a platelet-rich plasma that has been heat-treated according to the invention but that has not been activated before heat-treating, and a platelet-rich plasma that has been activated and then heat-treated according to the invention.
Figure 15:
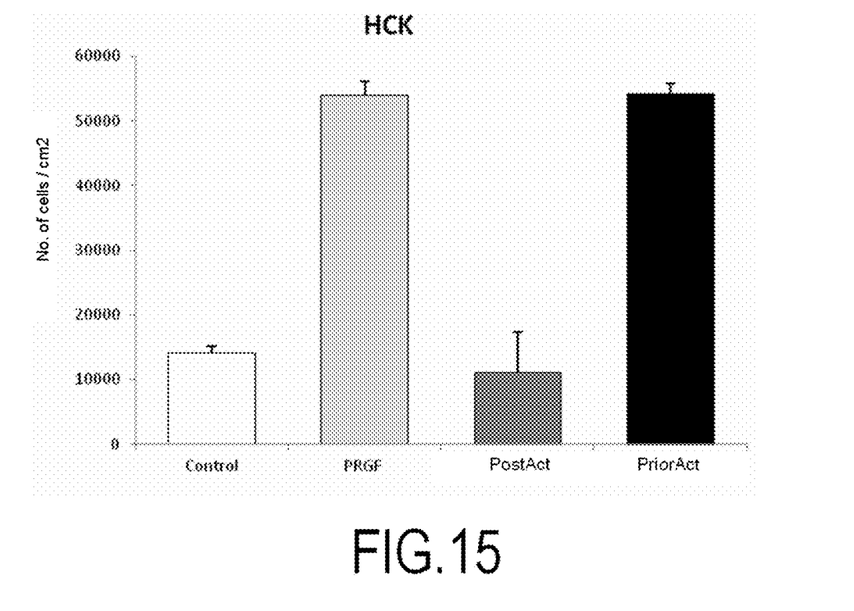
FIG. 15 shows a graph of the concentration of primary cell cultures of human corneal keratocytes (HCK), using the same media as in the case shown in the previous figure.
Figure 16:
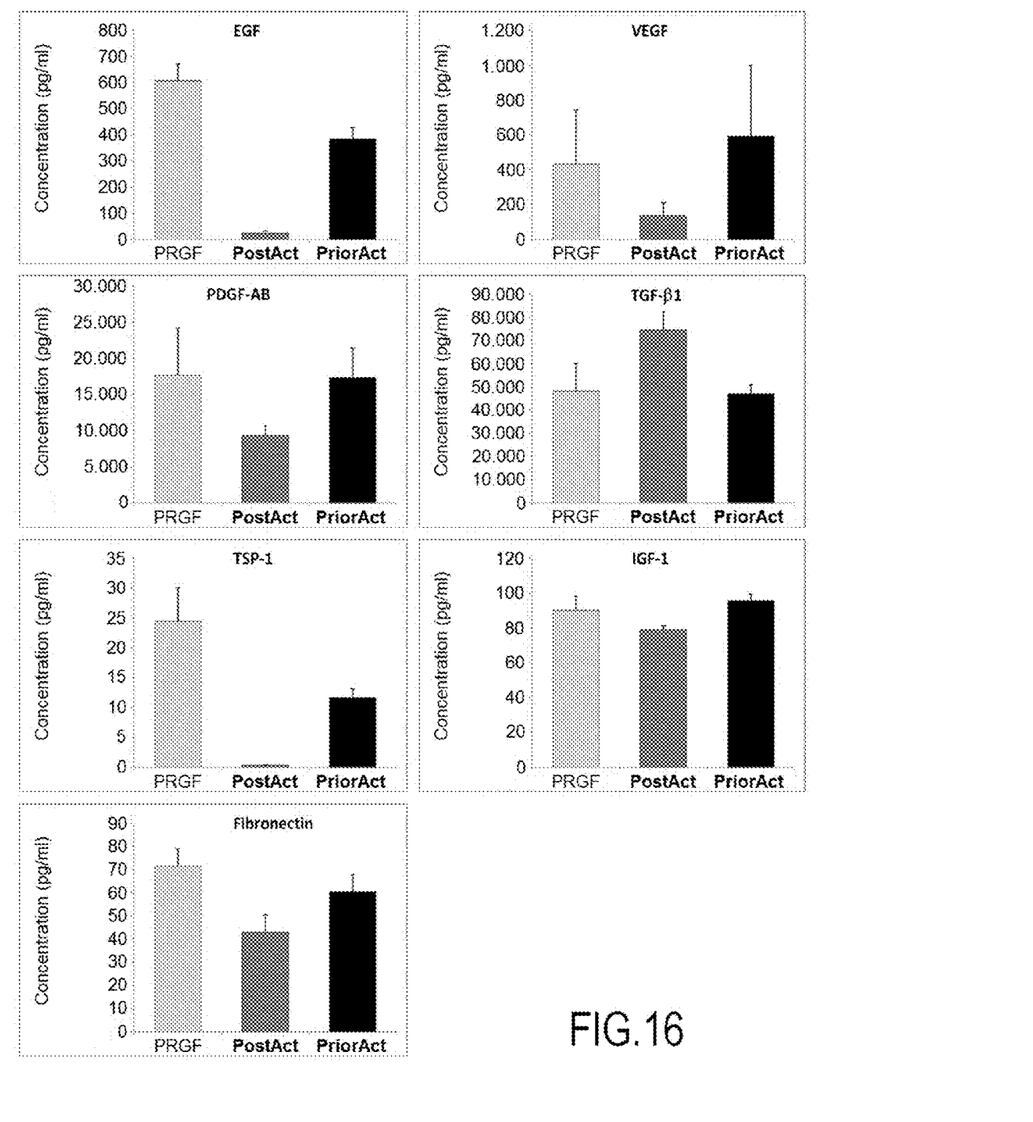
FIG. 16 shows several graphs of the concentration of different growth factors in the three compositions that served as cell culture media in the cases shown in the previous two figures.

The fact that the plasma or supernatant is initially activated, i.e. contains released growth factors prior to the heat treatment, provides surprising effects. On one hand, the plasma or supernatant obtained after activation and further heat treatment has a practically intact capability of aggregating and forming the fibrin clot. It also has an intact capability of freeing factors from their granular container. The fact that the capabilities of the plasma or supernatant remain unaffected can be understood from the data in FIGS. 14, 15 and 16. FIG. 14 shows a graph of the concentration of primary cell cultures of human conjunctival fibroblasts (HConF) performed in three different cell culture media: an activated platelet-rich plasma that has not been heat-treated (labelled "PRGF"), a platelet-rich plasma that has been heat-treated according to the invention but that has not been activated before heat-treating (labelled "PostAct"), and a platelet-rich plasma that has been activated and then heat-treated according to the invention (labelled "PriorAct"). As shown, cell proliferation is practically the same in case the present invention composition ("PriorAct") is used and in case the activated and non-heat-treated plasma ("PRGF") is used. Oppositely, cell proliferation is practically zero in case a platelet-rich plasma that has first been heat-treated and then activated ("PostAct") is used as a cell culture media. FIG. 15 shows a similar graph, but having grown human corneal keratocytes (HCK). FIG. 16 shows, in turn, different growth factor concentrations present in the different compositions, measure by means of ELISAs. As shown, growth factor concentration is practically the same in the platelet-rich plasma that has been activated and then heat-treated according to the invention (labelled "PriorAct") and in the activated and non-heat-treated plasma ("PRGF"). Oppositely, the platelet-rich plasma that has first been heat-treated and then activated ("PostAct") shows a global much worse growth factor concentration.

Lyophilizing is preferably performed without adding adjuvants (sugars such as trehalose, chemical components, etc.). Adjuvants are necessary for the lyophilizing of many substances, but it has been shown that plasmas or supernatants can be lyophilized without their help and that performing the lyophilization without adding any adjuvant results in a final dry composition (and thus a resuspended composition for its application to the patient) that has a higher biocompatibility. Some studies, for example, have demonstrated that certain adjuvants, like trehalose, have a negative impact on cell proliferation.

In addition, the procedure is characterized in that, in principle, there is no defined order for performing the steps of heat-treating and lyophilizing the plasma or supernatant. Nevertheless, it is preferable to perform the step of heat-treating before the step of lyophilizing the plasma or supernatant, as the product that is previously heat-treated will contain all its beneficial properties and potential, which is the aim of this process (reduction of complement and IgG), before being lyophilized. It is important to take into account that lyophilizing is carried out in order to improve the capacity of the compound to be preserved and stored, and therefore it is preferable that it constitute the final and not the initial stage. Thus, in summary, the first aim is to optimize the product and the second to improve its capacity for being preserved and stored.

The heat treatment may be any treatment that allows to appropriately increase the temperature of the plasma or supernatant, preferably to a temperature above 37° C. for a period of 1 minute or more. For example, the plasma or supernatant can be introduced into a water bath at said temperature and for said period of time. Given the fact that 37° C. is the temperature of the body as well as the temperature at which the complement and the immunoglobulins are at their maximum biologically active stage, it is preferable according to the invention that the plasma or supernatant be heated above 37° C. in order to achieve the elimination of some of the aforementioned components.

It is especially advantageous to subject the plasma or supernatant to a temperature between 50 and 60° C. (preferably at 56° C.), as at this temperature the components of the complement are optimally degraded and the protection of the proteins and growth factors contained in the product is maximized. Thus, it has been shown that temperatures below this range do not ensure that during incubation the complement is eliminated in the plasma or supernatant. On the other hand, incubation with temperatures above 60-65° C. would lead to the denaturation of the growth factors and the proteins contained in the plasma or supernatant. In addition to that, it is preferable that the plasma or supernatant be subjected to said temperature during 20 to 70 minutes (preferably between 30 to 60 minutes), as in this period of time the components of the complement are also optimally degraded and the protection of the proteins and growth factors contained in the product is also maximized.

The step of lyophilizing preferably comprises the following sub-steps:

freezing the plasma or supernatant to a temperature below 0° C.;

performing a first drying of the plasma or supernatant at a temperature below or equal to 0° C. and in high vacuum, during 1 minute or more and in a way that most of the free water contained in the plasma or supernatant is vaporised;

optionally, performing a second drying of the plasma or supernatant at a temperature above or equal to 0° C. and in high vacuum, low vacuum or no vacuum, during 1 minute or more and in a way that even the last traces of water vapour are eliminated, by evaporating the unfrozen water contained in the plasma or supernatant until reaching a final humidity of below 1%;

optionally, performing a third drying of the plasma or supernatant in a temperature above or equal to 0° C. and in high vacuum, low vacuum or no vacuum, during 1 minute or more and in a way that any residual humidity left in the product is eliminated through evaporation and its humidity content is reduced, thereby improving the stability of the final product.

It is especially advantageous to freeze the plasma or supernatant to a temperature between −60 and −40° C. (preferably at −50° C.) for more than 1 hour (preferably for more than 2 hours), as temperatures outside this range, especially lower freezing temperatures, increase the risk that the plasma or supernatant looses its biological properties as a result of the freezing. In addition to that, it is preferable that the blood compound be frozen for at least 1 hour in order to ensure that the blood compound is homogeneously frozen (this homogeneity guarantees the stability of the lyophilizing and that the product's biological properties are not altered).

As concerns the first drying, it is especially advantageous to perform it at a temperature between −60 and −40° C. and between 0.05 and 0.15 mBar (preferably at −50° C. and 0.1 mBar). Low temperature ranges are hereby used in order to ensure that the product is completely frozen during the process of sublimation, and to preserve the physical, chemical and biological properties of the initial product, thereby avoiding a potential denaturation of the lyophilized product's proteins. The exact duration of the process depends on the quantity of the product to be lyophilized and has been established for ensuring a complete sublimation of the ice that is necessary for an adequate drying.

As for the second drying, it is especially advantageous to perform it at a temperature between +15 and +25° C. and between 0.05 and 0.15 mBar (preferably at +20° C. and 0.1 mBar), as these conditions make it possible to eliminate any residual humidity left in the product through evaporation and to reduce its humidity content below 1% with the aim of improving the final product's stability.

Finally, it is especially advantageous to perform the third drying at a temperature between +15 and +25° C. and in high vacuum (preferably at +20° C. and in high vacuum), thereby eliminating any last traces of humidity and providing the final product with optimal characteristics in terms of uniformity and stability.

The procedure according to the invention may also comprise an additional step of filtering the plasma or supernatant in order to eliminate or avoid the presence of high molecular weight components, platelet aggregates or residues of fibrin that could affect the uniformity of the freezing process and the stability of the lyophilizing process, which in turn could have a negative impact on the resuspension of the dry composition (it should be taken into account that the dissolution rate of a lyophilized product is inversely proportional to the size of the particles it consists of, and that large particles contained in the dry composition could slow down the dissolution or even render it impossible). Should this additional process be performed, then the filtering of the plasma or supernatant is carried out before the lyophilizing, though not necessarily immediately before. On another note, the step of filtering the plasma or supernatant is not necessary if, for example, at the beginning of the procedure the plasma or supernatant has already been filtered.

Example of Procedure

An example of procedure is explained hereafter, showing the preparation of a final resuspended composition from a dry composition that in turn is obtained from a growth-factor-rich supernatant and performing the steps of the procedure according to invention.

Firstly, a growth-factor-rich plasma is prepared from blood extracted from a patient. For this purpose, the blood is centrifuged in order to separate it in various fractions, as known in prior art. Subsequently, the plasma fraction is extracted with the help of a PTD (Plasma Extraction Device) to a 9 ml fractionation tube. The plasma fraction is then activated; activation is carried out by estimating the plasma volume contained in the fractionation tube and subsequently adding 50 μl of PROF® Activator (en activator based on calcium chloride) per milliliter of plasma. Plasma activation is equivalent to saying that growth factors are released from the platelets contained in the plasma.

Secondly, the supernatant is obtained from the plasma rich in growth factors. For this purpose, the already activated growth-factor-rich plasma is incubated in a heating block at 37° C. for one hour to an hour and a half until the fibrin clot is completely retracted. Then, the fractionation tube is centrifuged at 1000 g during 10 minutes for two main reasons: to precipitate the fibrin clot that has formed and to extract the maximum volume possible of supernatant that may be retained within the clot. Thereafter, the centrifuged tubes are introduced in a laminar flow cabinet, where they may be opened to ensure the complete sterility of the sample. The released supernatant is collected with a 10 ml syringe attached with a blunt intramuscular needle. Then the needle is removed from the syringe, a 0.22 μm PVDF filter is attached and the supernatant is filtered. During the filtering process, the syringe with the filter is connected to multidose dispensers, administering 1 ml of filtered supernatant per device. Finally, the containers are hermetically sealed.

Next, the procedure according to the invention is executed in order to obtain a final dry composition from the filtered liquid supernatant. The multidose containers with the filtered supernatant are heat-treated by being introduced for 30 to 60 minutes into a water bath that has previously been heated to 56° C. After this period of time the containers are immediately introduced into a freeze dryer that has been cooled down to −50° C. in order to freeze them for a period of time between 2 to 8 hours depending on the volume of the supernatant and until the samples are homogeneously frozen. Afterwards, a first drying is performed at −50° C. and 0.1 mBar for a maximum of 24 hours. Then, a second drying is performed at +20° C. and 0.1 mBar for a maximum of 6 hours, followed by a third drying that is performed at +20° C. and in high vacuum for a maximum of 12 hours. The resulting product is a uniform and homogeneous powder that appears slightly compact and that can be simply and rapidly resuspended (i.e., dissolved and returned to its original consistency of a supernatant) when put in contact with an aqueous solution.

The final dry composition needs to be resuspended in order to be applied. Thus, the physician or the patient has to submerge a dose of the final dry composition in a predefined volume of sterile distilled water inside a container and then shake the container until the dry composition is completely dissolved in order to obtain a once again humid or liquid final composition. This final composition maintains all the biological properties of the original humid supernatant before it was heat-treated and lyophilized Said final composition can then be directly applied to the patient, for example as eye drops.

Experimental Results

Below are described the results of three experimental studies carried out on the procedure performed on a supernatant of plasma rich in growth factors and the composition obtained thereof according to the invention. The technical conclusions reached on said results are also detailed below.

1. Influence of the Heat Treatment Temperature on the Biological Effect and Growth-Factor Levels of the Final Dry Supernatant As mentioned, the heat treatment that is performed according to the invention at appropriate temperatures allows for the preservation of the supernatant's biological properties. In other words, the final dry composition substantially presents the same properties as the initial liquid supernatant.

Figure 1:
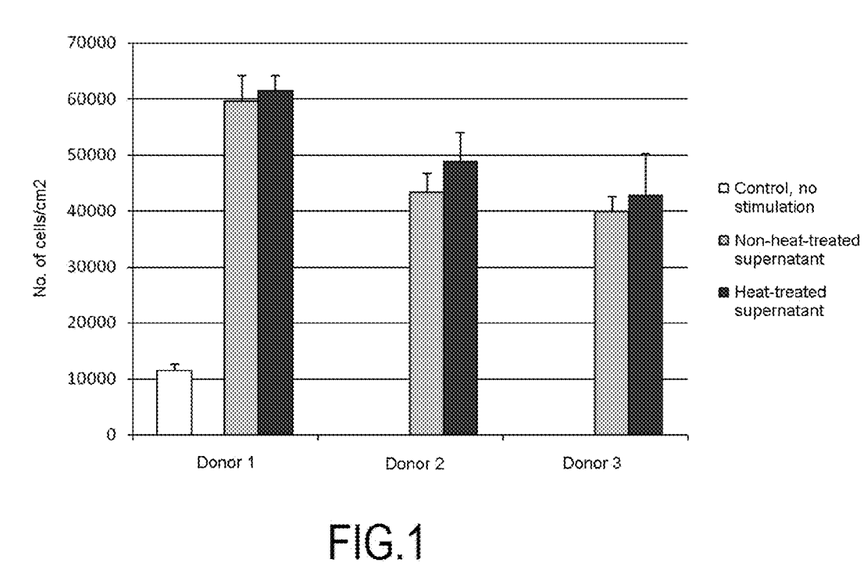
FIG. 1 shows a graph of the number of keratocytes (HCK) per square centimeter in three corneas treated with conventional supernatant plasma liquid that was not subjected to heat treatment, and with supernatant that was heat-treated according to the invention.

In relation to this, an experiment conducted on eye surface cell cultures showed that the heat treatment process (water bath at 56° C. during 30 minutes) did not affect the supernatant's biological effect on the proliferation of corneal keratocytes (HCK), conjunctival fibroblasts (HConF), and corneal epithelial cells. The multiplication of said cells in an in vitro culture was similar to the one of the supernatant that had not been heat-treated. This can be observed in FIG. 1, which shows the number of keratocytes (HCK) per square centimeter in three corneas, each treated with conventional supernatant plasma liquid that had not been subjected to heat treatment, and with a supernatant that had been heat-treated according to the invention. The proliferation of corneal keratocytes in response to the conventional supernatant plasma liquid that had not been subjected to heat treatment and in response to the supernatant that had been heat-treated according to the invention was practically equal. The same occurred in the case of the studied conjunctival fibroblasts and the corneal epithelial cells.

Figure 2:
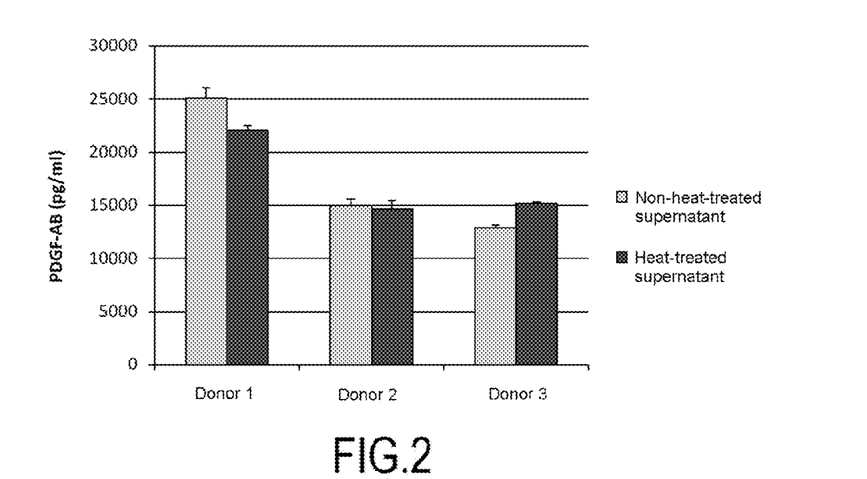
FIG. 2 shows a graph of the PDGF-AB levels in the supernatants of the three donors, before and after having been heat-treated according to the invention.
Figure 3:
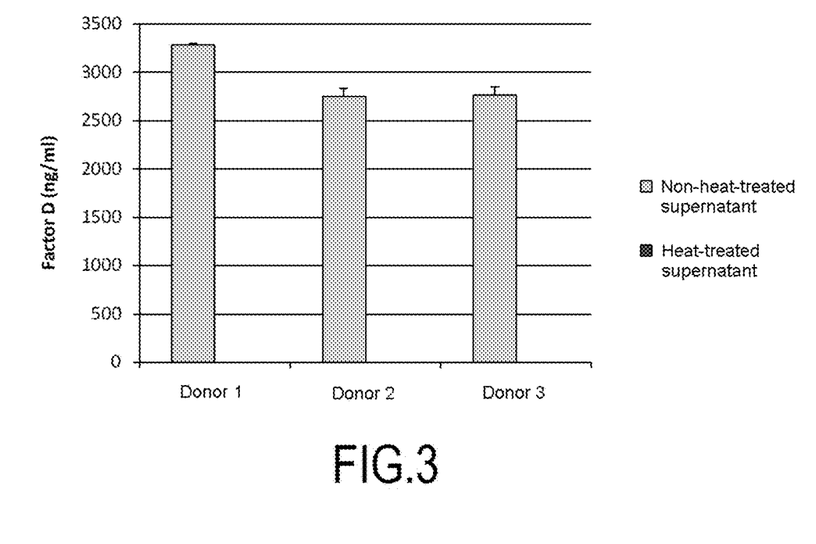
FIG. 3 shows the complement factor D levels in the supernatants of three donors, before and after having been heat-treated according to the invention.

An analysis was also carried out on the growth-factor levels present in the conventional supernatant liquids and the supernatants that had been heat-treated according to the invention. It was shown that, with regards to platelet factors PDGF-AB and TGF-β1, heat-treating did not affect their presence in the final supernatant. It was further shown that the analysed concentration of plasma growth factors such as the IGF-I was not changed by the applied temperature, whereas the values of other agents like the immunoglobulins G and M (IgG and IgM) had been reduced by 9% and 13% respectively. It was also shown that the complement factor D disappeared completely when the supernatant was subjected to heat treatment. Examples of these results can be seen in the following figures. For example, FIG. 2 shows the PDGF-AB levels in the supernatants of the three donors, before and after having been heat-treated according to the invention. As can be seen, said levels remained practically constant (in the first supernatant they slightly decreased, in the second one they remained constant and in the third one they slightly increased). FIG. 3, on the other hand, shows the complement factor D levels in the supernatants of the three donors, before and after having been heat-treated according to the invention. As can be observed, factor D was present in the initial supernatant liquids whereas it had completely disappeared in the heat-treated supernatants.

2. Influence of the Lyophilizing Process on the Biological Effect and the Growth-Factor Levels of the Supernatant As already mentioned in the present description, the process of lyophilizing performed according to the invention allows for the preservation of the supernatant's biological properties. In other words, the final dry composition substantially presents the same properties as the initial liquid supernatant.

Figure 4:
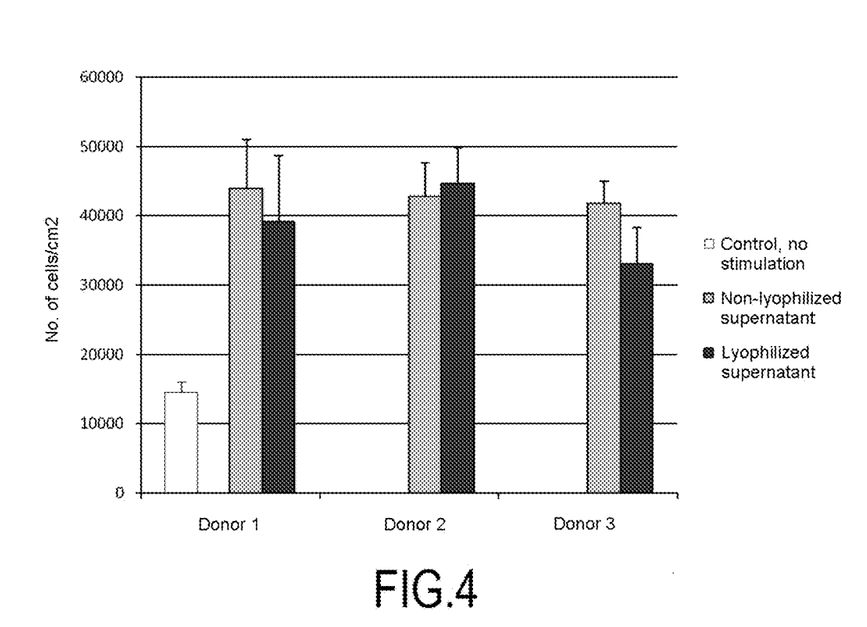
FIG. 4 shows a graph of the number of fibroblasts (HConF) per square centimeter in three corneas treated with conventional supernatant plasma liquid that was not subjected to heat treatment, and with supernatant that was heat-treated according to the invention.

The effect that lyophilizing the plasma supernatant had on the proliferation of conjunctival fibroblasts and keratocytes was analysed during experimentation. The results showed that lyophilization did not affect the growth of said cellular types in none of the three supernatants (of respective three donors) that were studied. This can be seen, for example, in FIG. 4 showing the number of fibroblasts (HConF) per square centimeter in three corneas treated with conventional supernatant plasma liquid that had not been subjected to heat treatment, and with supernatant that had been heat-treated according to the invention. The presence of fibroblasts remained relatively constant (in the first supernatant they slightly decreased, in the second one they slightly increased and in the third one they slightly decreased).

Figure 5:
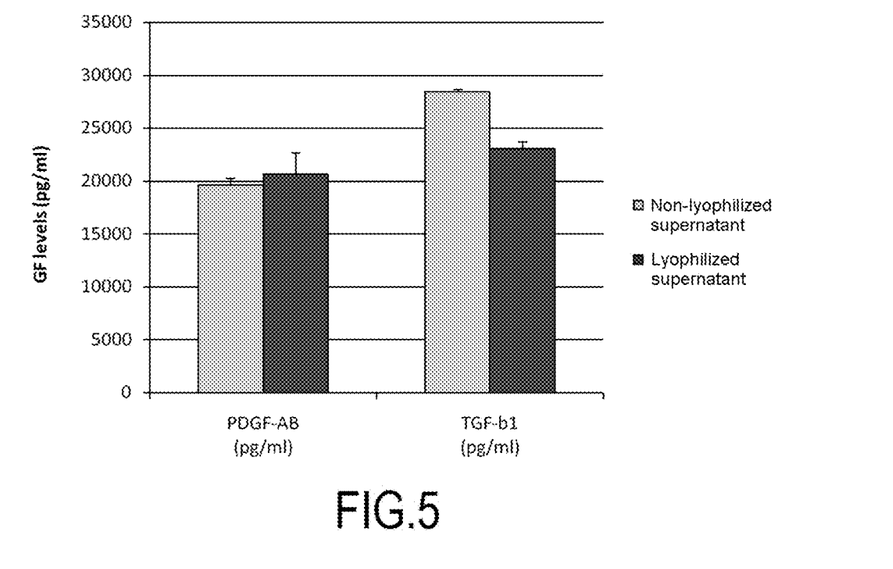
FIG. 5 shows a graph of the average concentration of the growth factors PDGF-AB and TGF-β1 in supernatants from three donors, both non-lyophilized and lyophilized according to the invention.
Figure 6:
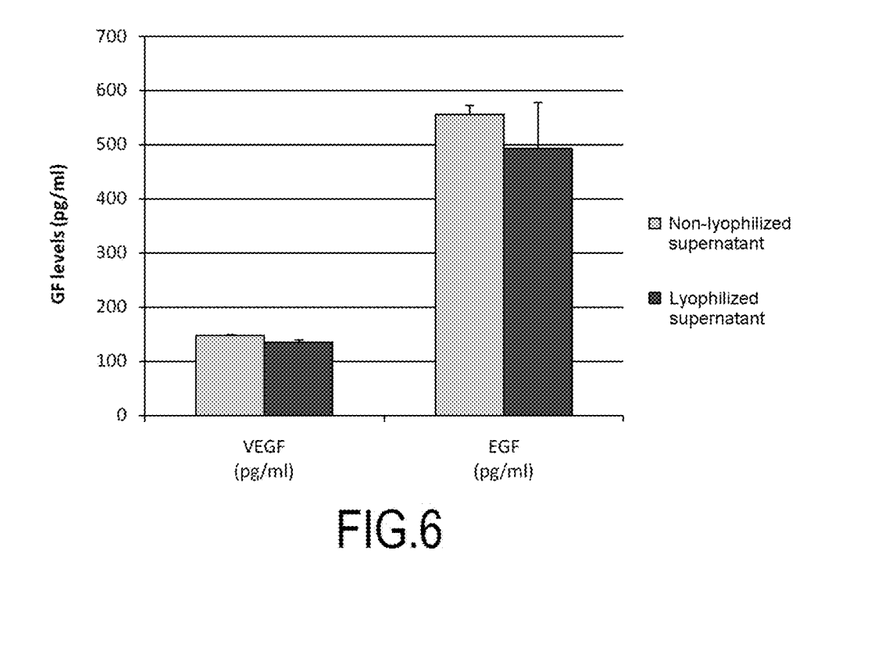
FIG. 6 shows a graph of the average concentration of the growth factors VEGF and EGF in supernatants from three donors, both non-lyophilized and lyophilized according to the invention.

An analysis was also carried out on the levels of growth factors present in the conventional supernatant liquids and the supernatants that had been lyophilized according to the invention. It was shown that the growth-factor levels did not change after lyophilizing. This applied to both platelet factors such as TGF-β1, PDGF-AB, VEGF and EGF as well as plasma factors such as IGF-I or the complement factor D. By way of example, FIG. 5 shows the average concentration of the growth factors PDGF-AB and TGF-β1 in three donors' supernatants which have been either non-lyophilized nor heat-treated or lyophilized and heat-treated according to the invention; it can be observed that the concentration of the former slightly increased, whereas the concentration of the latter slightly decreased but still remained significantly high. Similarly, FIG. 6 shows the concentration of the growth factors VEGF and EGF in three donors' supernatants which have been either non-lyophilized nor heat-treated or lyophilized and heat-treated according to the invention; it can be observed that the concentration of both factors slightly decreased, though it remained in high values.

3. Influence of the Filtering Process on the Biological Effect and the Growth-Factor Levels of the Supernatant It was also studied if filtering the supernatant could have any undesired biological effect on the supernatant, or if on the contrary, its biological properties remained unaltered.

In vitro studies showed that the process of filtering the supernatant did not modify the biological effect on the proliferation of conjunctival fibroblasts, keratocytes and corneal epithelial.

Figure 7:
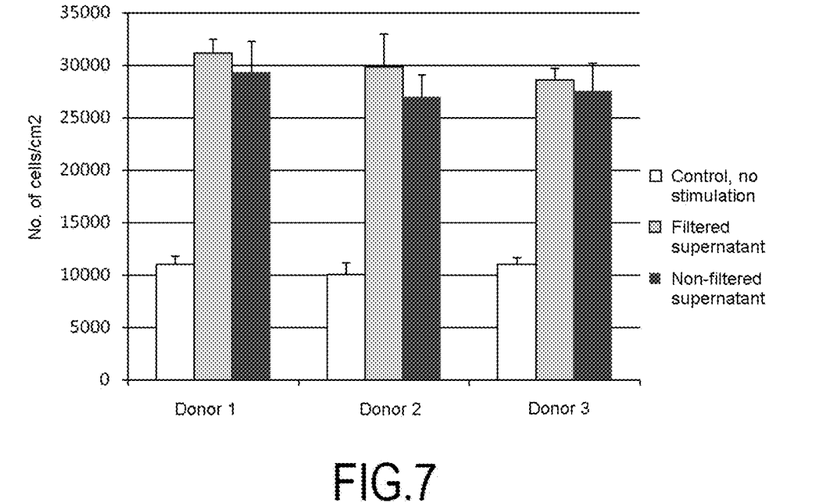
FIG. 7 shows a graph of the quantity of conjunctival fibroblasts (HConF) contained per square centimeter in three supernatant liquids, before and after having filtered said supernatants.

FIG. 7, for example, shows the quantity of conjunctival fibroblasts (HConF) contained per square centimeter in three supernatant liquids, before and after the supernatants were filtered. As can be observed, the proliferation of conjunctival fibroblasts in the filtered supernatant was similar to the one in the non-filtered supernatant.

Figure 8:
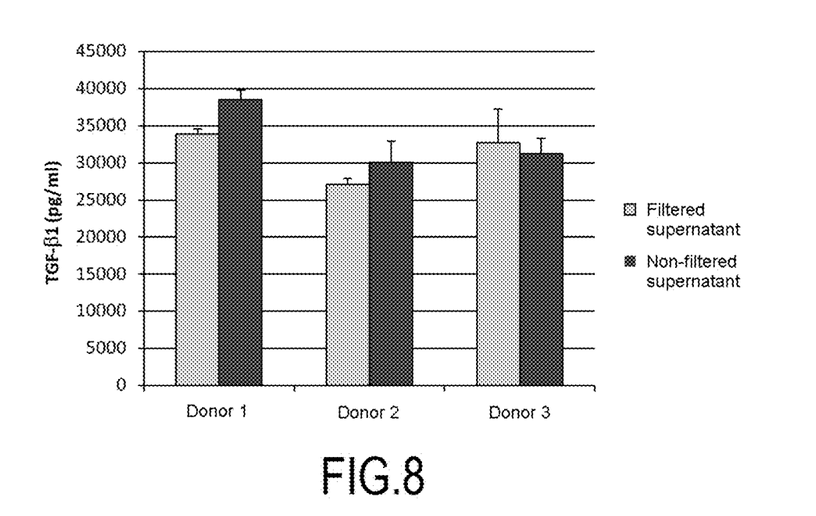
FIG. 8 shows a graph of the average concentration of the growth factor TGF-β1 in filtered and non-filtered supernatants.
Figure 9:
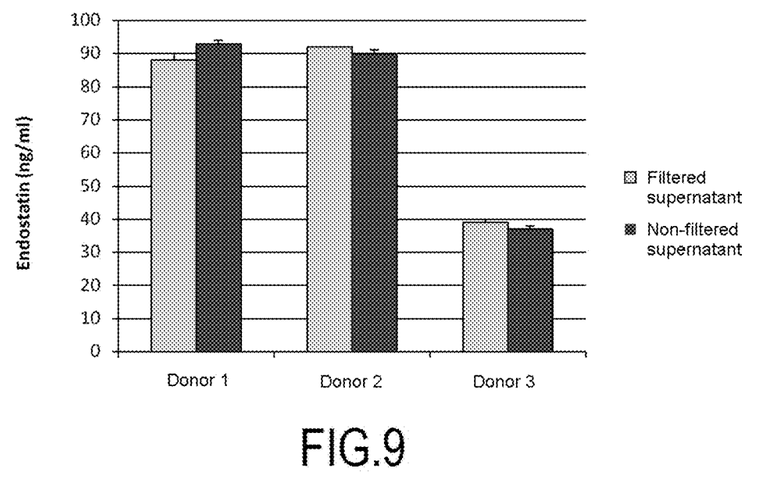
FIG. 9 shows a graph of the average concentration of the growth factor IGF-I in filtered and non-filtered supernatants.

With regard to the level of growth factors measured in the filtered and non-filtered supernatants, it was shown that they were similar in the three analysed supernatants (derived, as in all cases, from three different donors). FIG. 8 shows the average concentrations of the TGF-β1 growth factor in the filtered and non-filtered supernatants, giving evidence that the filtering of the supernatants did not significantly vary said concentrations. This fact does not solely apply to the growth factors contained in the platelet alpha-granules (e.g. TGF-β1, PDGF-AB, VEGF, EGF or TSP-1), but also to growth factors present in the plasma such as IGF-I (type 1 insulin-like growth factor) or endostatin. In this regard, FIG. 9 shows the average concentration of the growth factor IGF-I in the supernatant of the three donors, before and after having performed the filtering. As can be observed, the IGF-I level remained practically constant in all three cases.

Figure 10:
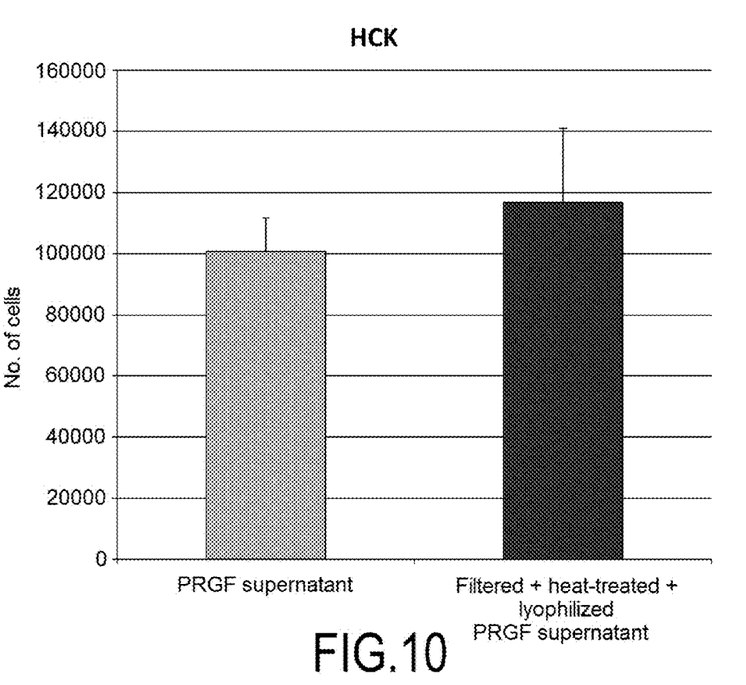
FIG. 10 shows a graph of the number of primary cells derived from human corneal keratocytes (HCK) after 72 hours of treatment with a conventional supernatant of plasma rich in growth factors (PRGF) and with a filtered, heat-treated, and lyophilized supernatant of plasma rich in growth factors (PRGF) according to the invention.

4. Influence of the Procedure According to the Invention, Comprising the Steps of Filtering, Heat-Treating and Lyophilizing, on Various Supernatant Properties FIG. 10 shows a graph of the proliferation of primary cells derived from human corneal keratocytes (HCK) after 72 hours of treatment with a conventional supernatant of growth-factor-rich plasma (PRGF supernatant), and with a filtered, heat-treated, lyophilized and subsequently resuspended PRGF supernatant according to the invention. As can be observed, the number of primary cells was slightly higher in the supernatant that was obtained by the procedure according to the invention.

Figure 11:
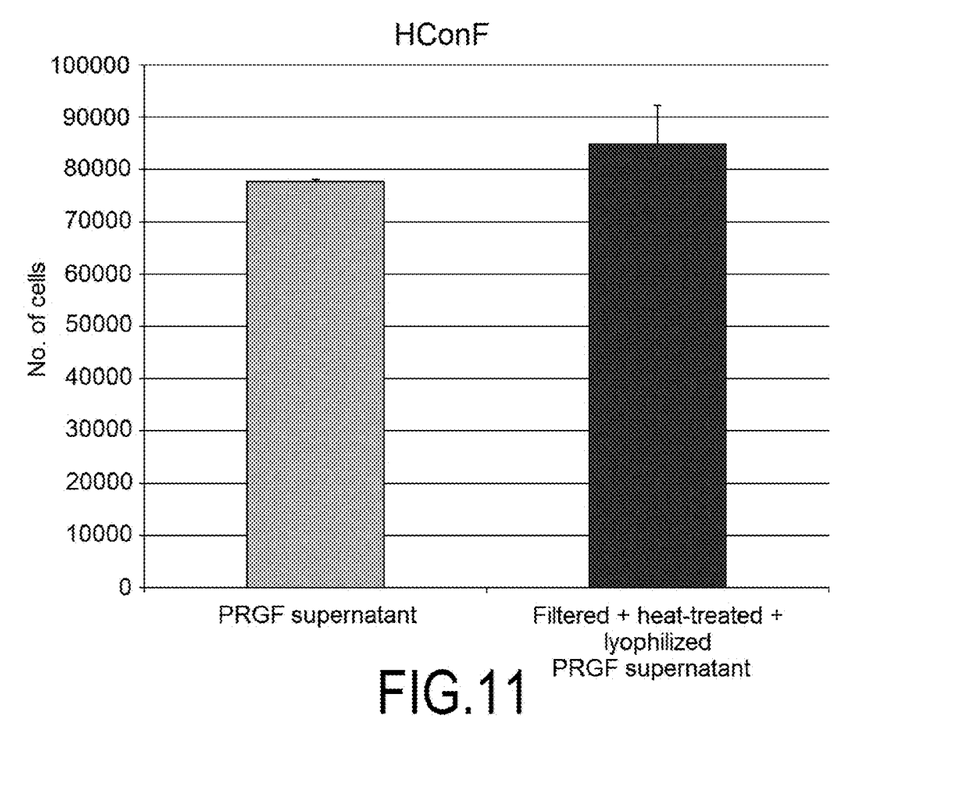
FIG. 11 shows a graph of the number of primary cells derived from human conjunctival fibroblasts (HConF) after 72 hours of treatment with a conventional supernatant of plasma rich in growth factors (PRGF) and with a filtered, heat-treated, and lyophilized supernatant of plasma rich in growth factors (PRGF) according to the invention, which has subsequently been re-suspended.

FIG. 11 shows a graph of the proliferation of primary cells derived from human conjunctival fibroblasts (HConF) after 72 hours of treatment with a conventional PRGF supernatant, and with a filtered, heat-treated, lyophilized and subsequently resuspended PRGF supernatant according to the invention. Just as in the previous graph, the number of primary cells was slightly higher in the supernatant that was obtained by the procedure according to the invention.

Figure 12:
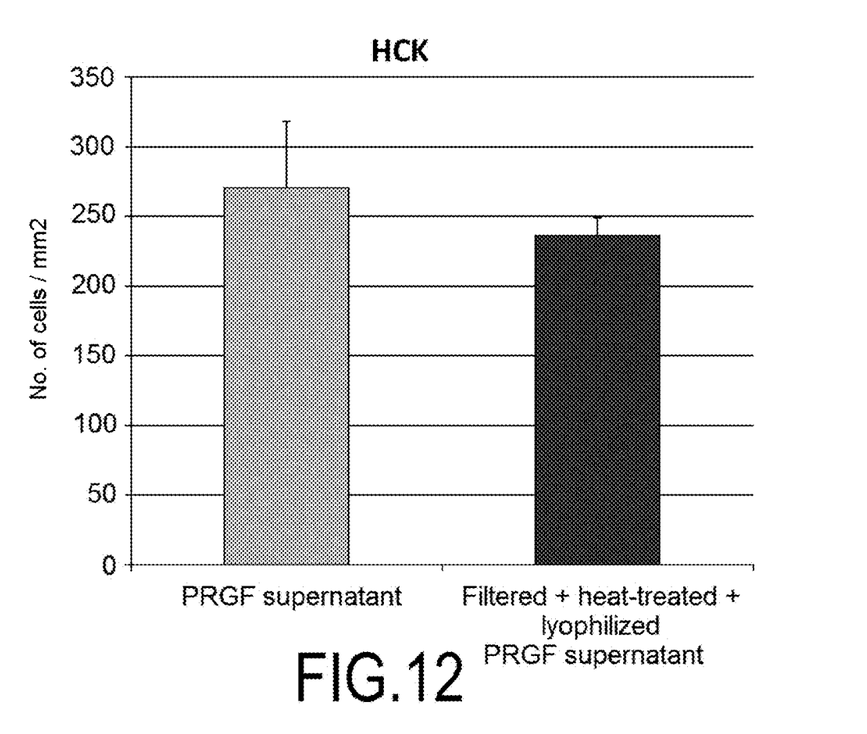
FIG. 12 shows a graph of the number of migrated cells in a human corneal keratocyte (HCK) cell culture after treatment with a conventional supernatant of plasma rich in growth factors (PRGF) and with a filtered, heat-treated, and lyophilized supernatant of plasma rich in growth factors (PRGF) according to the invention, which has subsequently been re-suspended.

FIG. 12 shows the effect of the application of a conventional PRGF supernatant and of a filtered, heat-treated, lyophilized and subsequently resuspended PRGF supernatant according to the invention, on the migration of the primary cell culture from human corneal keratocytes (HCK). As can be observed, the number of primary cells is only slightly higher in case that a conventional supernatant is used as growth medium.

Figure 13:
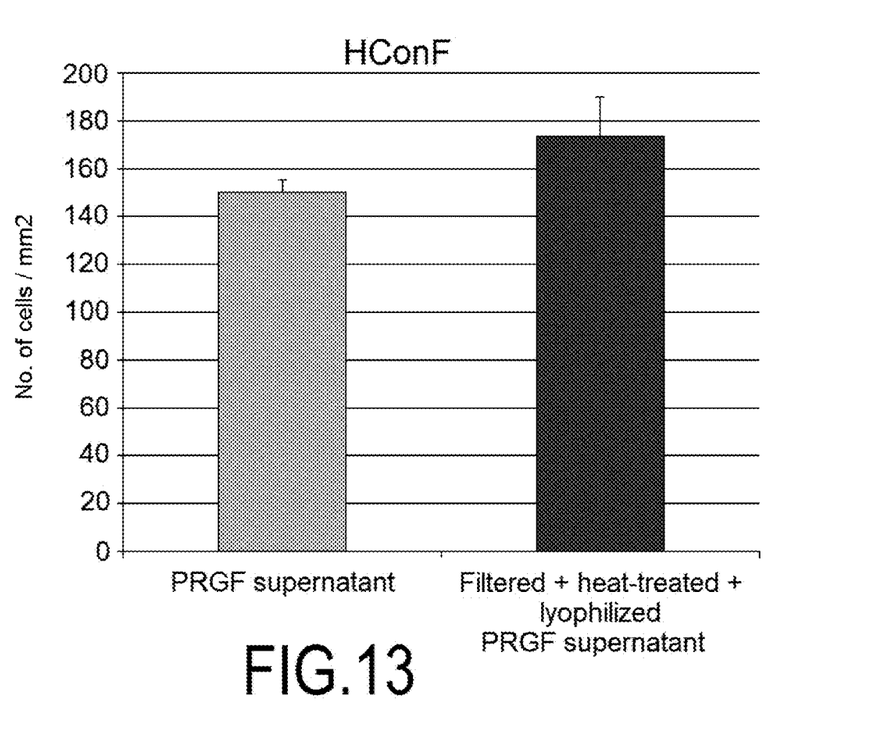
FIG. 13 shows a graph of the number of migrated cells in a conjunctival fibroblast (HCF) cell culture after treatment with a conventional supernatant of plasma rich in growth factors (PRGF) and with a filtered, heat-treated, and lyophilized supernatant of plasma rich in growth factors (PRGF) according to the invention, which has subsequently been re-suspended.

FIG. 13 shows the effect of the application of a conventional PRGF supernatant and of a filtered, heat-treated, lyophilized and subsequently resuspended PRGF supernatant according to the invention, on the migration of the primary cell culture from human conjunctival fibroblasts (HConF) after having carried out a 24-hour cell incubation. As can be seen, the behaviour in both cases was quite similar, although the results of the supernatant obtained according to the invention were somewhat better.

In summary, and after having analysed all the graphs of the experimental results, it may be concluded that the behaviour and the properties of the final resuspended composition are very similar (with slight inconsequential variations) to the behaviour and properties of the conventional supernatant requiring immediate application. Therefore, it may be concluded that, on the one hand, the fact of filtering, heat-treating and lyophilizing a humid supernatant in order to obtain a dry resuspendable product does not affect the product's properties and, on the other hand, it provides the numerous benefits listed in the present document.

The invention claimed is:

1. A process for obtaining a composition containing growth factors that comprises the steps of:
   (a) providing a platelet-rich plasma that contains platelet-released growth factors or a supernatant thereof that contains platelet-released growth factors, and then either
   (I)
   (b) subjecting the platelet-released growth factor-containing platelet-rich plasma or supernatant to heat treatment, whereby the temperature of the platelet-rich plasma or supernatant is increased, and
   (c) lyophilizing the heat treated platelet-released growth factor-containing platelet-rich plasma or supernatant of (I)(b), or,
   (II)
   (b') lyophilizing the platelet-released growth factor-containing platelet-rich plasma or supernatant, thereby obtaining a lyophilizate and
   (c') subjecting the lyophilizate of (b') to heat treatment, whereby the temperature of the lyophilizate is increased,
   wherein said providing step (a) comprises contacting a platelet-rich plasma or supernatant thereof with a coagulation activating agent in order to artificially induce release of growth factors, whereby growth factors are released by said platelets, thus obtaining said platelet-rich plasma or said supernatant that contains released growth factors,
   wherein lyophilization of (I)(c) or (II)(b') is the first lyophilization to which said plasma or supernatant was subjected, and
   wherein, in said heat treatment of (I) (b) or (II)(c'),
   the platelet-rich plasma or the supernatant of a platelet-rich plasma of (I) or the lyophilizate of (II) is subjected to a temperature between 50 and 60° C. for 20 to 70 minutes.

2. The process of claim 1, wherein lyophilization is performed without adding adjuvants.

3. The process of claim 1, wherein (I) applies.

4. The process of claim 1, wherein
   said heat treatment comprises subjecting the platelet-rich plasma or the supernatant of a platelet-rich plasma to a temperature of 56° C. for 30 to 60 minutes.

5. The process of claim 1, wherein the step of lyophilizing comprises the steps of:
   freezing the platelet-rich plasma or the supernatant of a platelet-rich plasma to a temperature below 0° C., and
   performing a first drying of the platelet-rich plasma or the supernatant of a platelet-rich plasma at a temperature below or equal to 0° C. and in high vacuum, during 1 minute or more.

6. The process of claim 5, wherein:
   the platelet-rich plasma or the supernatant of a platelet-rich plasma is frozen to a temperature between −60 and −40° C. for more than 1 hour, and
   the first drying of the platelet-rich plasma or the supernatant of a platelet-rich plasma is performed at a temperature between −60 and −40° C. and at a pressure between 0.05 and 0.15 mBar.

7. The process of claim 6, wherein:
   the freezing of the platelet-rich plasma or the supernatant of a platelet-rich plasma is performed at the temperature of −50° C. for more than 2 hours, and
   the first drying of the platelet-rich plasma or the supernatant of a platelet-rich plasma is performed at the temperature of −50° C. and at the pressure of 0.1 mBar.

8. The process of claim 5, wherein the step of lyophilizing comprises the additional step of:
   performing a second drying of the platelet-rich plasma or the supernatant of a platelet-rich plasma in a temperature above or equal to 0° C. and in high vacuum, during 1 minute or more.

9. The process of claim 8, wherein:
   the second drying of the platelet-rich plasma or the supernatant of a platelet-rich plasma is performed at a temperature between +15 and +25° C. and at a pressure between 0.05 and 0.15 mBar.

10. The process of claim 9, wherein:
    the second drying of the platelet-rich plasma or the supernatant of a platelet-rich plasma is performed at a temperature of +20° C. and a pressure of 0.1 mBar.

11. The process of claim 5, wherein the step of lyophilizing comprises the additional step of:
    performing a second drying of the platelet-rich plasma or the supernatant of a platelet-rich plasma in a temperature above or equal to 0° C. and in low vacuum or no vacuum, during 1 minute or more.

12. The process of claim 8, wherein the process comprises the additional step of:
    performing a third drying of the platelet-rich plasma or the supernatant of a platelet-rich plasma in a temperature above or equal to 0° C. and in high vacuum, during 1 minute or more.

13. The process of claim 12, wherein:
    the third drying of the platelet-rich plasma or the supernatant of a platelet-rich plasma is performed at a temperature between +15 and +25° C. and in high vacuum.

14. The process of claim 13, wherein:
    the third drying of the platelet-rich plasma or the supernatant of a platelet-rich plasma is performed at +20° C. and in high vacuum.

15. The process of claim 8, wherein the process comprises the additional step of:
    performing a third drying of the platelet-rich plasma or the supernatant of a platelet-rich plasma in a temperature above or equal to 0° C. and in low vacuum or no vacuum, during 1 minute or more.

16. The process of claim 1, wherein the process comprises the additional step of filtering the platelet-rich plasma or the supernatant of a platelet-rich plasma, which is performed before lyophilization.

17. The process of claim 1 wherein, as a result of said heat treatment, the level of complement and/or immunoglobulins in said plasma or supernatant, or in said lyophilizate thereof, is reduced.

18. A process for obtaining a composition containing growth factors that comprises the steps of:
    (a) providing a platelet-rich plasma that contains platelet-released growth factors or a supernatant thereof that contains platelet-released growth factors, and then either
    (I)
    (b) subjecting the platelet-released growth factor-containing platelet-rich plasma or supernatant to heat treatment, whereby the temperature of the platelet-rich plasma or supernatant is increased, and (c) lyophilizing the heat treated platelet-released growth factor-containing platelet-rich plasma or supernatant of (I)(b), or, (II)

(b') lyophilizing the platelet-released growth factor-containing platelet-rich plasma or supernatant, thereby obtaining a lyophilizate and (c') subjecting the lyophilizate of (b') to heat treatment, whereby the temperature of the lyophilizate is increased, wherein, in said heat treatment of (I)(b) or (II) (c'), the platelet-rich plasma or the supernatant of a platelet-rich plasma of (I) or the lyophilizate of (II) is subjected to a temperature between 50 and 60° C. for 20 to 70 minutes.

* * * * *